(12) United States Patent
Dodds et al.

(10) Patent No.: US 7,799,532 B2
(45) Date of Patent: *Sep. 21, 2010

(54) DETECTION AND MEASUREMENT OF THYROID HORMONE AUTOANTIBODIES

(75) Inventors: W. Jean Dodds, Santa Monica, CA (US); Ferdie S. Ongchangco, Upland, CA (US)

(73) Assignee: Hemopet, Garden Grove, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/269,866

(22) Filed: Nov. 12, 2008

(65) Prior Publication Data

US 2010/0120170 A1 May 13, 2010

(51) Int. Cl.
G01N 33/53 (2006.01)

(52) U.S. Cl. ............... 435/7.1; 435/7.92; 435/7.93; 435/7.94; 436/500; 436/506

(58) Field of Classification Search ............ 436/500
See application file for complete search history.

(56) References Cited

U.S. PATENT DOCUMENTS

| | | | |
|---|---|---|---|
| 3,995,019 A | 11/1976 | Jerome | |
| 4,855,242 A | 8/1989 | Soeldner | |
| 5,691,157 A | 11/1997 | Gong et al. | |
| 5,817,025 A | 10/1998 | Alekseev et al. | |
| 5,830,709 A | 11/1998 | Benson et al. | |
| 5,911,687 A | 6/1999 | Sato et al. | |
| 5,954,640 A | 9/1999 | Szabo | |
| 6,018,786 A | 1/2000 | Krick et al. | |
| 6,063,028 A | 5/2000 | Luciano | |
| 6,081,786 A | 6/2000 | Barry et al. | |
| 6,135,055 A | 10/2000 | Pratt | |
| 6,136,055 A | 10/2000 | Stanek | |
| 6,218,122 B1 | 4/2001 | Friend et al. | |
| 6,232,522 B1 | 5/2001 | Harley et al. | |
| 6,287,254 B1 | 9/2001 | Dodds | |
| 6,358,546 B1 | 3/2002 | Bebiak et al. | |
| 6,537,213 B2 | 3/2003 | Dodds | |
| 6,730,023 B1 | 5/2004 | Dodds | |
| 7,029,441 B2 | 4/2006 | Dodds | |
| 7,134,995 B2 | 11/2006 | Dodds | |
| 7,548,839 B2 | 6/2009 | Dodds | |
| 7,552,039 B2 | 6/2009 | Dodds | |
| 2002/0022772 A1 | 2/2002 | Dodds | |
| 2003/0135096 A1 | 7/2003 | Dodds | |
| 2005/0090718 A1 | 4/2005 | Dodds | |

OTHER PUBLICATIONS

Young et al., Characterization of Canine Triiodothyronine (T3) Autoantibodies and Their Effect on Total T3 in Canine Serum, Proceedings of the Society for Experimental Biology and Medicine, 188, 1988, pp. 219-228.*

Patzl et al., Determination of Autoantibodies to Thyroglobulin Thyroxine and Triiodothyronine in Canine Serum, J. Vet. Med. A 50, 2003, pp. 72-78.*

Laurberg et al., Sensitive assay for thyroglobuling autoantibodies in serum employing polyethylene glycol for precipitation, Scand J Clin Lab Invest 1988; 48: pp. 137-140.*

Jensen, et al., "Evaluation of Thyroid Function in Dogs by Hormone Analysis: Effects of Data on Biological Variation", Veterinary Clinical Pathology, vol. 25, No. 4, 1996 (5 pages).

Lurye, et al., "Evaluation of an In-House Enzyme-Linked Immunosorbent Assay for Quantitative Measurement of Serum Total Thyroxine Concentration in Dogs and Cats", Scientific Reports: Original Study, JAVMA, vol. 221, No. 2, Jul. 15, 2002 (7 pages).

Horney, et al., "Evaluation of an Automated, Homogeneous Enzyme Immunoassay for Serum Thyroxine Measurement in Dog and Cat Serum", Veterinary Clinical Pathology, vol. 28, No. 1, 1999 (9 pages).

Weeks, et al., "Acridinium Esters as High-Specific-Activity Labels in Immunoassay", Clinical Chemistry, vol. 29, No. 8, 1983 (6 pages).

Dudley, "Chemiluminescence Immunoassay: An Alternative to RIA", Laboratory Medicine, vol. 21, No. 4, Apr. 1990 (7 pages).

Dodds, "Autoimmune Thyroid Disease", DOG World, vol. 77, No. 4, Apr. 1992 (4 pages).

Van Der Watt, et al., "Euthyroid Patient with Elevated Serum Free Thyroxine", Clinical Chemistry, 54:1239-1241, Jul. 2008 (6 pages).

Kellogg, et al., "A Girl with Goiter and Inappropriate Thyroid-Stimulating Hormone Secretion", Clinical Chemistry, 54:1241-1244, Jul. 2008 (6 pages).

Kricka, "Commentary", Clinical Chemistry, 54:1245, Jul. 2008 (2 pages).

Burman, "Commentary", Clinical Chemistry, 54:1246, Jul. 2008 (2 pages).

Evason et al., Alterations in thyroid hormone concentrations in healthy sled dogs before and after athletic conditioning, American Journal of Veterinary Research, (Mar. 2004) vol. 65, No. 3, pp. 333-337.

O'Kelly et al., Thyroid hormone concentrations in the plasma of fed and fasted Brahman and Hereford steers, Australian Journal of Experimental Agriculture, 1994, 34 pp. 439-442.

Bogicevic et al., Thyroid Hormone Profiles in Experimental Acute Renal Failure, Renal Failure, 15(2), 1993, pp. 173-179.

Panciera et al., Thyroid Function in Dogs with Spontaneious and Induced Congestive Heart Failure, Can J Vet Res 1994; 58: pp. 157-162.

Young et al., The Relationship Between Autoantibodies to Triiodothyronine (T3) and Thryoglobulin (Tg) in the Dog, Autoimmunity, 1991, vol. 9, pp. 41-46.

Antech Diagnostics, Assessing Thyroid Function, Antech Diagnostics News, Nov. 2005, pp. 1-5.

* cited by examiner

*Primary Examiner*—Melanie J. Yu
*Assistant Examiner*—Gary W Counts
(74) *Attorney, Agent, or Firm*—Greenberg Traurig LLP

(57) ABSTRACT

A non-radioisotopic method detects T3AA and T4AA thyroid autoantibodies in a sample from a non-human species such as the canine species. Antibodies and autoantibodies are bound, and a precipitated or bound antigen-antibody or antigen-autoantibody complex is formed. The supernatant or surrounding fluid of the bound or precipitated antigen-antibody or antigen-autoantibody complex is then removed. The thyroid activity of the bound complex, precipitate, supernatant or surrounding fluid is measured. The thyroid analyte is at least one of T3, Free T3, T4 or Free T4.

13 Claims, No Drawings

DETECTION AND MEASUREMENT OF THYROID HORMONE AUTOANTIBODIES

BACKGROUND

This disclosure is directed to the qualitative and quantitative detection of thyroid autoantibodies in non-human species.

The laboratory diagnosis of autoimmune thyroid disease is determined by demonstrating elevated levels of autoantibodies directed against thyroid hormones and related proteins in serum or plasma. Measurement of thyroid autoantibodies in serum by radioimmunoassay (RIA) is currently an important clinical diagnostic and research tool to determine whether an individual is affected with autoimmune thyroid disease, one of the most common endocrine disorders of humans and domestic animals.

Thus, as physicians and veterinary clinicians have become increasingly aware of the prevalence of thyroid disorders, the demand for practical and inexpensive screening tests for thyroid dysfunction has arisen. Currently the RIA procedures require equipment that needs labor intensive operation, potentially toxic reagents, sophisticated technology, and skilled technologists. These tests are labor-intensive assays which increase the actual and retail cost of the assay.

There is a need within the field for sensitive assays which are quantitative, specific, safe and easy to perform, and have increased efficiency.

No simple, safe immunological screening assay for the autoimmune type of thyroid disorders has been available in the form of sophisticated quantitative assays of thyroid hormones.

Radioimmunoassay methods are presently used to measure thyroid-autoantibodies in humans and the non-human species.

A disadvantage of the above assay methods is their dependency on the use of radioisotopes, which are no longer considered safe for users or the environment.

SUMMARY

A solution to these problems is provided in this disclosure.

The present disclosure provides an assay for determining T3AA or T4AA thyroid-autoantibodies in non-human species which is easy to perform, safe, efficient, and accurate using non-radioisotopic and non-radioimmune detection methods.

For example, in one assay configuration a serum sample from a non-human species is contacted with a thyroid antibody, thus allowing the thyroid antigen present in the sample to bind to the antibody and form an anitgen:antibody complex. The complex is detected with a non-radioisotopic method such as a chemiluminescence assay (CLA) or an electroluminescence assay (ELA).

Antigen or antibody is added to the aliquot of the serum sample and then is treated in a manner that causes precipitation or substrate binding or electrophoretic migration of any thyroid antibody present in the sample. The resulting precipitate or substrate bound complex is separated from the supernatant or surrounding fluid by centrifugation or migration, and then the remaining supernatant or surrounding fluid is contacted a second time with a thyroid antibody and the amount of thyroid antigen:antibody complex is measured.

Alternatively, the amount of the precipitate or substrate bound complex is measured in like manner.

The difference between the thyroid antibody:antigen complex level in treated serum samples is quantitated, and represents the amount of thyroid antibody or autoantibody present in the individual serum sample for the non-human species.

Other features and advantages of the disclosure will be apparent from the following description of the embodiments thereof, and from the claims.

DESCRIPTION

The following embodiments according to the disclosure are given as an example only, without being limiting in any way.

This disclosure addresses disadvantages of prior art systems. This disclosure also relates to an assay system which avoids the need of radioimmune assay systems.

Thyroid dysfunction caused by autoimmune thyroiditis which leads to hypothyroidism is the most common endocrine disorder of canines. The heritable form of canine autoimmune, lymphocytic thyroiditis is very prevalent and present in at least 50 breeds of purebred dogs and their crossbreeds or mixed breeds. An estimated 90% of thyroid disease in those dogs is due to the autoimmune form of the disorder.

There is a need, therefore, for sensitive and specific diagnostic tests for the thyroid hormones and also for the thyroid autoantibodies, the presence of which is the hallmark of heritable autoimmune thyroiditis. Diagnosis of autoimmune thyroiditis is important for clinical identification, management and treatment of affected individual animals, as well as for genetic screening in purebred animal populations to improve the overall health and longevity of affected breeds.

In humans, sensitive assays for thyroid autoantibodies exist for measuring thyroglobulin (anti-TG) and thyroid peroxidase (anti-TPO), and for antibodies to the thyroid stimulating hormone receptor (Anti-TSHR). Most of these specific human assays for autoimmune thyroiditis use radioisotopes, although direct chemiluminescent techniques are also available. Autoantibodies to T3 (anti-T3) and T4 (anti-T4) are not measured in humans.

By contrast, autoimmune thyroiditis in dogs is diagnosed by measuring anti-T3 and anti-T4 (also known as T3AA and T4AA autoantibodies) as well as thyroglobulin autoantibody (TgAA) in serum. No clinical diagnostic tests are available for anti-TPO and anti-TSHR in dogs or other animals because these autoantibodies either have not been detected in animals with thyroiditis (anti-TSHR) or are present infrequently or in low levels in affected individuals (anti-TPO). This is a major difference between diagnosing human and canine autoimmune thyroid disease.

While measurement of anti-TG is commercially available in dogs and uses a non-radioisotopic electroimmunosorbent assay (ELISA) method, until the present disclosure, no non-radioisotopic test for anti-T3 and anti-T4 antibodies (T3AA and T4AA, respectively) is known or available. There is a need for non-radioisotopic assays for measuring T3AA and T4AA with high sensitivity, and this has not been known before the present disclosure.

In one aspect of the disclosure, there is a method of detecting non-radio isotopic T3AA thyroid autoantibodies in a sample from a non-human species, particularly a canine, which comprises precipitating the antigen-antibody or antigen-autoantibody complex. The precipitated antigen-antibody or antigen-autoantibody complex is separated from the supernatant or surrounding fluid; and the thyroid activity of the precipitate or supernatant or surrounding fluid is measured, where the thyroid analyte is T3 or Free T3.

In another aspect of the disclosure, there is a method of detecting non-radio isotopic T4AA thyroid autoantibodies in a sample from a non-human species, particularly a canine, which comprises precipitating the antigen-antibody or antigen-autoantibody complex. The precipitated antigen-antibody or antigen-autoantibody complex is separated from the supernatant or surrounding fluid; and the thyroid activity of the precipitate or supernatant or surrounding fluid is measured, where the thyroid analyte is T4 or Free T4.

Non-radioisotopic detection of autoimmune thyroid autoantibodies is effected. A chemical or substance can bind or precipitate the antigen:antibody complex. This can be either charcoal or polyethylene glycol or other substances or particles.

Detection of either the supernatant or surrounding fluid after precipitation or binding or removal of the antigen-antibody or antigen-autoantibody complex is made.

Alternatively, the antigen-antibody or antigen-autoantibody complex itself is measured in the precipitate or detachable bound complex. The measuring can be by fluorescence, or chemical or other tagging, or measuring of the mass.

The method for determining the quantity of an autoantibody in a sample comprises the steps of:

(1) providing a non-radioisotopic labeled antigen or antibody;

(2) contacting the non-radioisotopic labeled antigen with the sample in solution to form a non-radioisotopic labeled antigen-antibody or an antigen-autoantibody complex;

(3) providing an agent for precipitating or binding of the complex;

(4) mixing the solution containing the non-radioisotopic labeled antigen-antibody or an antigen-autoantibody complex with the precipitating or binding agent to produce a precipitate or bound complex, and a supernatant or surrounding fluid. The supernatant or surrounding fluid contains uncomplexed non-radioisotopic labeled antigen and the precipitate or bound complex contains the non-radioisotopic labeled antigen-autoantibody complex and uncomplexed non-radioisotopic labeled antigen; and (5) measuring the quantity of non-radioisotopic label in the precipitate or bound complex in a manner substantially independent of the amount of uncomplexed non-radioisotopic labeled antigen in the precipitate or bound complex by:

(a) measuring the quantity of the label in the precipitate or bound complex;

(b) determining the quantity of the uncomplexed non-radioisotopic labeled antigen present in the precipitate or bound complex by (i) providing a control sample that is substantially identical to the test sample, (ii) providing an non-radioisotopic unlabelled antigen to the antibody or autoantibody, (iii) contacting the control sample in solution with the non-radioisotopic unlabelled antigen or antibody to form an unlabelled antigen-autoantibody or antigen-antibody complex, (iv) contacting the solution containing the unlabelled antigen-antibody or antigen-autoantibody complex with the non-radioisotopic labeled antigen to the antibody or autoantibody, the quantity of the non-radioisotopic labeled antigen added being the same as the quantity added in step (2), (v) mixing the solution containing the unlabelled antigen-antibody or antigen-autoantibody complex with a quantity of the precipitating or binding agent used in step (4) to cause a precipitate or bound complex to form, the precipitate or bound complex containing the unlabelled antigen-antibody or antigen-autoantibody complex, the unlabelled antigen, and the non-radioisotopic labeled antigen, the labeled antigen being present in the same quantity as in the precipitate or bound complex formed in step (4), and (vi) providing a measurement of the quantity of non-radioisotopic label in the precipitate or bound complex; and (c) determining the quantity of the antibody or autoantibody in the sample by subtracting the result of step (b) from the result of step (a) and relating the difference in quantity of the non-radioisotopic label in the precipitate or bound complex to the quantity of the antibody or autoantibody in the sample.

The quantity of the unlabelled antigen contacted with the control sample in step (iii) is sufficient to preclude essentially the non-radioisotopic labeled antigen contacted in step (iv) from forming a non-radioisotopic labeled antigen-antibody or antigen-autoantibody complex.

In some cases the quantity of the unlabelled antigen is at least as great as or greater than the quantity of the non-radioisotopic labeled antigen.

The sample can be serum, and the autoantibody can be thyroid autoantibody, and the antigen can be thyroid hormone.

The precipitate or bound complex formed in step (4) can be washed at least twice with a washing agent to dissolve the uncomplexed labeled antigen without dissolving the non-radioisotopic labeled antigen-antibody or antigen-autoantibody complex. The precipitate or bound complex formed in step (5)(b)(v) can be washed at least twice with a washing agent to dissolve the uncomplexed labeled antigen without dissolving the non-radioisotopic labeled antigen-antibody or antigen-autoantibody complex.

The washing would reduce the amount of the uncomplexed labeled antigen to less than 5% of the total amount of label in the precipitate or bound complex.

The supernatant or surrounding fluid after precipitation or binding and removal of the precipitate or bound complex can be detected, or the precipitate or detachable bound complex, itself is measured. The measuring of the precipitate or detectable bound complex is by fluorescence, or non-radioisotopic tagging, or measuring the mass of the bound complex.

Technology

A system is used that employs direct CLA technology and can employ different bioluminescent detectors such as oxyluciferin, luminol, isoluminol and acridinium ester, and different microparticles such as latex, polystyrene, gold or paramagnetic materials as a solid phase.

An example is described with acridinium ester (AE) as the label and paramagnetic particles (PMP) as a solid phase. This chemiluminescence technology procedure requires an additional signal amplification or additional substrate using base and acid reagents, and the result is a rapid emission of light and minimal background noise. The random access immunoassay system has a throughput of up to about 180 tests per hour in batch or random access mode.

CLA is a chemical reaction that emits energy in the form of light. When used in combination with immunoassay technology, the light produced by the reaction indicates the amount of analyte in a sample. Direct CLA reactions directly measure the light energy without the use of added steps or amplifying molecules. The assays use AE as the CLA label, which uses the addition of a catalyst or substrate to initiate the chemiluminescence reaction.

Direct CLA using AE is automated and provides many benefits, such as long reagent shelf-life, fast reaction time, and assay sensitivity. The assays use the dimethyl form of AE since its stability allows long reagent shelf-life.

AE is oxidized by hydrogen peroxide and the light emission is maximized by changing the environment from acidic to basic. Oxidation of AE occurs rapidly, with peak light emission within one second. The rapid reaction time and low background make direct CLA with AE faster than RIA or ELA methods.

Assay Reaction Formats

The assay system directly measures the amount of light that the chemiluminescent reaction emits. The system uses a variety of formats to detect antigens as well as antibodies. The system applies the immunoassay binding principles of antibodies using any one of several different formats:

sandwich format
competitive format
antibody-capture format

Antibody binding principles are known and are established on the basis that antibodies are proteins that are produced by the immune system in response to an antigen. Antibodies are ideal for use in immunoassays because they can be produced to bind to specific antigens. In immunoassays, the antigen is the analyte that is being measured.

AE can be covalently bound to an antibody or antigen without altering the ability of the autoantibodies to bind to an antigen or antibody, respectively.

PMP are iron oxide crystals that are attracted to a magnetic field. In the assays, PMP coated with antibodies or antigen provide a solid phase reactive surface. Coated PMP provide approximately 50 times the reactive surface area of coated tubes or beads.

During incubation, coated PMP bind to the target antigen or antibody. When exposed to a magnetic field, the PMP bound to antigen or antibody are drawn toward the magnets. While the magnets hold the PMP in place, sample and reagent not bound to the coated PMP are washed away.

Acid and base reagents are added to initiate the CLA reaction. The emission of light is measured in relative light units (RLUs). Once the light produced from the oxidation of AE is quantified, the system calculates the concentration of antigen.

In a sandwich format, the analyte-specific antigen concentration in the sample and the light emission has a direct relationship. If more analyte-specific antigen molecules are present in the sample, then more AE is present, and light emission is therefore greater.

If the sample has a low concentration of analyte-specific antigen, most binding sites on the antibody are bound to AE-labeled antigen. This results in an elevated reading of RLUs from the oxidation of AE.

If the sample has a high concentration of analyte-specific antigen, most binding sites on the antibody are bound to antigen from the sample, and few sites are bound to AE-labeled antigen. This results in a lower reading of RLUs from the oxidation of the AE.

In a competitive assay with AE-labeled antigen or antibody, the concentration of antigen or antibody in the sample and the light emission have an inverse relationship.

Antigen bound to PMP competes with analyte-specific antigen in the sample for limited binding sites on AE-labeled antibody. If more analyte-specific antigen is present in the sample, then less PMP-labeled antigen is bound. Alternatively, if less analyte-specific antigen is present in the sample then more PMP-labeled antigen is bound.

The antibody-capture format is used when the substance being measured in the sample is an antibody. The assay uses a reagent containing an additional antibody that is specifically directed against the antibody in the sample.

In this example of an antibody-capture assay, the sample concentration and the light emission have a direct relationship. If more antibody is present, then more AE is present, and therefore the light emission is higher.

In general, the disclosure features a method for determining the quantity of an autoantibody in a sample, the method having the steps of: (1) providing a non-radioisotopic labeled antigen; (2) contacting the labeled antigen with the sample in solution to form a labeled antigen-antibody or antigen-autoantibody complex; (3) providing an agent for precipitating or binding the complex; (4) mixing the solution containing the labeled antigen-antibody or antigen-autoantibody complex with the precipitating or binding agent to produce a precipitate or bound complex and a supernatant or surrounding fluid, the supernatant or surrounding fluid containing labeled antigen and the precipitate containing the labeled antigen-antibody or antigen-autoantibody complex possibly contaminated with uncomplexed non-radioisotopic labeled antigen; and (5) measuring the quantity of non-radioisotopic label in the precipitate or bound complex or the supernatant and surrounding fluid in a manner substantially independent of the amount of any contaminating uncomplexed non-radioisotopic labeled antigen in the precipitate.

The disclosure can include the steps of: (a) measuring the quantity of the non-radioisotopic label in the precipitate or bound complex; (b) determining the quantity of the non-radioisotopic label in the precipitate or bound complex not attributable to the non-radioisotopic labeled antigen-antibody or antigen-autoantibody complex; and (c) determining the quantity of the antibody or autoantibody in the sample by subtracting the result of step (b) from the result of step (a). In step (b), the quantity of the uncomplexed non-radioisotopic labeled antigen present in the precipitate or bound complex is determined by (i) providing a control sample that is identical to the sample; (ii) providing an unlabelled antigen to the antibody or autoantibody; (iii) contacting the control sample in solution with the unlabelled antigen to form an unlabelled antigen-antibody or antigen-autoantibody complex; (iv) contacting the solution containing the unlabelled antigen-antibody or antigen-autoantibody complex with the non-radioisotopic labeled antigen to the autoantibodies, the quantity of the non-radioisotopic labeled antigen added being the same as the quantity added in step (2); (v) mixing the solution containing the unlabelled antigen-antibody-autoantibodies complex with the same quantity of the precipitating or binding agent used in step (4) to cause a precipitate or bound complex to form, the precipitate containing the unlabelled antigen-antibody-autoantibodies complex, possibly contaminated with unlabelled antigen, and possibly contaminated with non-radioisotopic labeled antigen, the non-radioisotopic labeled antigen being present in the same quantity as in the precipitate or bound complex formed in step (4); and (vi) providing a measurement of the quantity of label in the precipitate or bound complex; wherein the quantity of the unlabelled antigen contacted with the control sample in step (iii) is sufficient to preclude substantially all the non-radioisotopic labeled antigen contacted in step (iv) from forming a non-radioisotopic labeled antigen-antibody or antigen-autoantibody complex.

The disclosure can include the steps of: (a) providing a control sample that is identical to the sample; (b) providing an unlabelled antigen to the antibody or autoantibody; (c) contacting the control sample in solution with the unlabelled antigen to form an unlabelled antigen-antibody or antigen-autoantibody complex; (d) contacting the solution containing the unlabelled antigen-antibody or antigen-autoantibody complex with labeled antigen to the antibody or autoantibody, the quantity of the non-radioisotopic labeled antigen added being the same as the quantity added in step (2); (e) mixing the solution containing the unlabelled antigen-antibody or antigen-autoantibody complex with the same quantity of the precipitating or binding agent used in step (4) to produce a precipitate or bound complex and a supernatant or surrounding fluid, the precipitate or bound complex containing the unlabelled antigen-antibody or antigen-autoantibody complex, unlabelled antigen, and non-radioisotopic labeled antigen, the non-radioisotopic labeled antigen being present in the same quantity as in the precipitate or bound complex formed in step (4); (f) providing a measurement of the quantity of the label in the supernatant or surrounding fluid produced in step (e); (g) providing a measurement of the quantity of the label in the supernatant produced in step (4); and (h) determining the quantity of the antibody or autoantibody in the precipitate or bond complex by subtracting the result of step (g) from the result of step (f); wherein the quantity of the unlabelled antigen contacted with the control sample in step (iii) is sufficient to preclude substantially all the non-radioisotopic labeled antigen contacted in step (iv) from forming a labeled antigen-antibody or antigen-autoantibody complex.

The sample is serum; and the autoantibodies are thyroid autoantibodies. In a particular embodiment where the autoantibodies are thyroid autoantibodies, the antigen is thyroid hormone, and the amount of the non-radioisotopic labeled thyroid antigen contacted with the serum in step (2) is between 0.2-15 micrograms of labeled non-radioisotopic thyroid per deciliter of serum.

In another aspect, there is a method for determining the quantity of autoantibodies in a body fluid or tissue, the method having the steps of: (1) providing a controlled amount of non-radioisotopic labeled antigen to the antibody or autoantibody, the controlled amount not substantially exceeding the amount of natural antigen present in the body fluid; (2) contacting the non-radioisotopic labeled antigen with the body fluid to form a labeled antigen-antibody or antigen-autoantibody complex; (3) providing an agent for precipitating or binding the complex; (4) mixing the solution containing the complex with the precipitating or binding agent to produce a precipitate or bound complex and a supernatant or surrounding fluid, the precipitate or bound complex containing non-radioisotopic labeled antigen-antibody-autoantibodies complex; and (5) measuring the quantity of label in the precipitate or bound complex or the supernatant or surrounding fluid.

In another aspect, the disclosure features a method for determining the quantity of an autoantibody in a sample, such as body fluid or tissue extract, the method having the steps of: (1) providing a non-radioisotopic labeled antigen to the antibody or autoantibodies; (2) contacting the labeled non-radioisotopic antigen with the sample in solution to form a labeled antigen-antibody-autoantibodies complex; (3) providing an agent for precipitating or binding the complex; (4) mixing the solution containing the non-radioisotopic labeled antigen-antibody or antigen-autoantibody complex with the precipitating or binding agent to produce a precipitate or bound complex and a supernatant or surrounding fluid, the precipitate or bound complex containing the non-radioisotopic labeled antigen-antibody or antigen-autoantibody complex and uncomplexed non-radioisotopic labeled antigen; (5) washing the precipitate or bound complex at least twice with a washing agent to remove uncomplexed non-radioisotopic labeled antigen without dissolving non-radioisotopic labeled antigen-antibody or antibody-autoantibody complex, the supernatant or surrounding fluid from the first washing being combined with the supernatant or surrounding fluid produced in step (4); and (6) measuring the quantity of label in the precipitate or bond complex in the combined supernatants or surrounding fluids.

In different embodiments, the washing reduces the amount of non-radioisotopic labeled antigen in the precipitate to less than 5% of the total amount of label in the precipitate or bound complex; the autoantibodies are thyroid autoantibodies; the washing agent is 7-25% polyethylene glycol or other suitable fluids; the sample is serum; the antigen is thyroid hormone; and the amount of the non-radioisotopic labeled thyroid contacted with the serum in step (2) is between 0.2-15 micrograms of non-radioisotopic labeled thyroid antigen per deciliter of serum.

In another aspect, the disclosure features a method for determining the quantity of an autoantibodies in a body fluid or tissue, the method having the steps of: (1) providing a non-radioisotopic labeled antigen to the antibody or autoantibody; (2) contacting the non-radioisotopic labeled antigen with the body fluid and incubating the resultant solution for a period sufficient to allow substantially all naturally present antigen to dissociate from the antibody or autoantibody and to form a non-radioisotopic labeled antigen-antibody or antigen-autoantibody complex; (3) providing an agent for precipitating or binding the complex; (4) mixing the solution containing the non-radioisotopic labeled antigen-antibody or antigen-antigen-autoantibody complex with the precipitating or binding agent to produce a precipitate or bound complex and a supernatant or surrounding fluid, the supernatant or surrounding fluid containing uncomplexed non-radioisotopic labeled antigen and the precipitate or bound complex containing the non-radioisotopic labeled antigen-antibody or antigen-autoantibody complex and uncomplexed non-radioisotopic labeled antigen; and (5) measuring the quantity of label in the precipitate or bound complex or the supernatant or the surrounding fluid.

In different embodiments, the body fluid is serum, and the autoantibodies are thyroid autoantibodies, the antigen is thyroid hormone, and the incubation period is 15-90 minutes.

In another aspect, the disclosure features a method of diagnosing thyroid disease in a non-human being prior to their being clinically diagnosed as having thyroid disease, the method having the steps of: (1) providing a serum sample of the non-human, the serum sample containing hormone or other protein autoantibodies (e.g., autoantibodies to thyroid hormone); (2) providing non-radioisotopic labeled hormone or other protein (e.g., thyroid hormone); (3) contacting the non-radioisotopic labeled hormone or other protein with the serum to form a non-radioisotopic labeled hormone or other protein-hormone or other protein autoantibody complex; (4) providing an agent for precipitating or binding the complex; (5) mixing the solution containing the complex with the precipitating or binding agent to produce a precipitate or bound complex, and a supernatant or surrounding fluid, the precipitate or bound complex containing the non-radioisotopic labeled complex; (6) measuring the quantity of label in the precipitate or bound complex, the quantity indicating the quantity of the hormone autoantibodies in the serum; (7) comparing the quantity of hormone autoantibodies in the serum to a pre-determined threshold level; and (8) diagnosing the thyroid disease if the quantity of the autoantibodies in the serum is higher than the pre-determined threshold level.

Detection of Thyroid Hormone Autoantibodies

In the radioimmunoassay (RIA) method, the patient's serum is incubated with radiolabeled triiodothyronine (T3) or thyroxine (T4) or freeT3 or freeT4 and barbital buffer containing inhibitors, such as 8-anili-no-1-naphthalene-sulfonic acid or salicylates, which act to prevent thyroid hormones from binding to their binding proteins. This step is typically followed either by precipitation of gamma globulin or by absorption of free radioactive thyroid hormone.

The present disclosure uses a non-radioimmunoassay technique as described.

T3 and T4 Autoantibodies Non-Radioistopic Procedure

The following is a method for the detection of antithyroid hormone autoantibodies.

(1) Measure the amount of T3 or freeT3 and T4 or freeT4 in the serum of patient (unknown) specimens, preferably in duplicate. These are the pre-treatment serum samples.

(2) Pipette another aliquot of sample into a test tube labeled with the specimen accession number and T3 or freeT3.

(3) Add an aliquot of the T3 or freeT3 antibody.

(4) Repeat steps (2) and (3) adding another aliquot of specimen labeled T4 or freeT4, and add an aliquot of T4 or freeT4 antibody.

(5) Cover the specimen tubes and mix in Vortex or other mixer.

(6) Incubate all specimen tubes in a waterbath or heating block at a temperature range of 25-50 degrees C. for an incubation range of 15-90 minutes.

(7) Remove specimens from the waterbath or heating block, add a precipitating or binding agent such as polyethylene glycol (PEG) or charcoal or other substance or particle, and incubate at room temperature for 15-90 minutes.

(8) Centrifuge the mixture at a speed range of 1500-4500 rpm at a temperature range of 2-10 degrees C. for a time range of 10-30 minutes.

(9) Aspirate the supernatant fluids, and add to test tubes labeled with the specimen accession number and analyte measured.

(10) Re-suspend the precipitates or bound antigen:antibody complexes in distilled water or other eluting agent, mix, and then measure the T3 or freeT3 and T4 or freeT4 is the accessioned treated specimens, as was done in Step (1).

(11) Add distilled water or other fluid to the supernatants to dilute them from 2-5 times, mix, and then measure the T3 or freeT3 and T4 or freeT4 is the accessioned treated specimens, as was done in Step (1).

(12) Calculate the average amount of T3 or freeT3 and T4 or freeT4 in the duplicate pre-treatment patient specimens.

(13) Calculate the average amount of T3 or freeT3 and T4 or freeT4 in the duplicate post-treatment specimens after treatment outlined in Steps (2)-(11).

(14) Subtract the results obtained in Step (13) from those in Step (12) to obtain the amount of T3 autoantibody and T4 autoantibody, and record in Relative Antibody Units (RAU).

(15) Repeat Steps (2)-(14) using known Control specimens from healthy individuals and known Thyroiditis specimens from patients with documented autoimmune thyroiditis.

Standards and Controls: Non-human sera obtained from healthy (normal) individuals is pooled for the pooled as negative control. Normal sera are defined as having T4<3.0 micrograms/deciliter and T3<200 nanograms/deciliter. Positive control patient sera with elevated thyroid autoantibodies is also pooled, when it is available. Controls are aliquotted and frozen, and are thawed and used once. The autoantibody levels in the positive control specimens will tend to decrease over time despite freezing of the specimens.

Example Results: T3 and T4 Autoantibody Non-Radioisoptic Procedure

The results of the disclosed system for measurement in comparison to other measuring systems are set out.

In the following tables, Table 1 compares the current normal ranges for healthy dogs established by two reference laboratories, namely, Michigan State University Diagnostic Center for Population and Animal Health and Antech Diagnostics, using RIA techniques, with those established by direct CLA of the present disclosure, measured at Hemopet/Hemolife.

Table 2 compares the established background autoantibody cut-off levels for healthy normal dogs (negative autoantibody control cut-off levels) at Michigan State University, Antech Diagnostics, and Hemopet/Hemolife.

Table 3 lists examples of negative autoantibody cut-off data from four healthy normal dogs and the mean results for these four animals listed in RAU.

Table 4 compares results for T3 and T4 autoantibody (T3AA and T4AA, respectively) expressed in RAU from six dogs with autoimmune thyroiditis measured at Antech Diagnostics with RIA and at Hemopet/Hemolife with the CLA method of the present disclosure. All six samples are positive for both T3AA and T4AA except sample #5 which is positive for T3AA but negative (below negative control cut-off level) for T4AA.

TABLE 1

Normal Canine Thyroid Analytes Measured By Radioimmunoassay (RIA) and Chemiluminescence (CLA)

| ANALYTES | RIA (Michigan State University; S.I. units) | RIAs (Antech Diagnostics; Standard Units) | CLA (Present Disclosure; Standard Units) |
|---|---|---|---|
| T3 | 1-2.5 nmol/L | 45-150 ng/dL | 30-70 ng/dL |
| Free T3 | 4.5-12 pmol/L | 1.7-5.3 pg/mL | 1.6-3.5 pg/mL |
| T4 | 15-67 nmol/L | 1-4 µg/dL | 0.8-3.8 µg/dL |
| Free T4 | 8-26 pmol/L | 0.4-2.06 ng/dL | 0.6-2.5 ng/dL |

TABLE 2

Negative Autoantibody Normal Control Dogs

| Canine Normal | Using RIA and CLA Disclosed Methods | T3AA (RAU) NORMAL | T4AA (RAU) NORMAL |
|---|---|---|---|
| RIA Method | Michigan State University Diagnostic Center | <10 | <20 |
| RIA method | Antech Diagnostics | <2.0 | <2.0 |
| CLA Disclosed Method | Hemopet/Hemolife | <1.4 | <0.9 |

TABLE 3

Example Data from Normal Control Dogs Using CLA Disclosed Method

| Canine Normal Samples | T3AA (RAU) | T4AA (RAU) |
|---|---|---|
| 1. | 1.7 | 0.9 |
| 2. | 1.2 | 0.9 |
| 3. | 1.4 | 0.3 |
| 4. | 0.7 | 1.1 |
| Mean Result | 1.3 | 0.8 |

TABLE 4

Example Data from Dogs with Autoimmune Thyroiditis (Positive T3 and/or T4 Autoantibody) Example Thyroiditis Data Using RIA Method versus CLA Disclosed Method

| Canine Thyroditis Serum Samples | Antech RIA T3AA RAU) | Hemolife CLA T3AA (RAU) | Antech RIA T4AA (RAU) | Hemolife CLA T4AA (RAU) |
|---|---|---|---|---|
| 5 | 2.5 | 2.4 | 1.2 | 0.8 |
| 6 | 3.8 | 2.9 | 2.3 | 1.6 |
| 7 | 8.0 | 5.3 | 7.2 | 4.4 |

TABLE 4-continued

Example Data from Dogs with Autoimmune Thyroiditis
(Positive T3 and/or T4 Autoantibody)
Example Thyroiditis Data Using RIA Method versus
CLA Disclosed Method

| Canine Thyroditis Serum Samples | Antech RIA T3AA RAU) | Hemolife CLA T3AA (RAU) | Antech RIA T4AA (RAU) | Hemolife CLA T4AA (RAU) |
|---|---|---|---|---|
| 8 | 2.6 | 1.9 | 3.2 | 2.9 |
| 9 | 4.6 | 3.5 | 5.5 | 3.0 |
| 10 | 4.2 | 5.8 | 2.2 | 1.0 |

RIA = radioimmunoassay;
CLA = chemiluminescence;
RAU = relative antibody units.

The present disclosure achieves these assays with a direct chemiluminescence technique having a sensitivity of 1 femtogram ($10^{-15}$ g) per mL. This is significantly more sensitive than RIA assays that have a sensitivity of 1 picogram ($10^{-12}$ g) per mL. The non-RIA assays of the present disclosure also provide an assay system and reagent technique with improved safety and shelf-life.

The above Tables 3 and 4 are examples of measuring circulating T3 and T4 autoantibodies.

OTHER EMBODIMENTS

Other embodiments are within the scope of the disclosure.

For example, other precipitating agents can be used, such as either ammonium sulfate or hydrochloric acid in ethanol. Moreover, other antibodies can be detected by the methods of this disclosure. For example, antigenic determinants for islet cell autoantibodies can be isolated from islets of Langerhans, labeled radioisotopically or non-radioisotopically, and then used to assay for islet cell autoantibodies in serum.

In addition to dogs, the assay of the subject disclosure can quantitatively determine levels in many other domestic and laboratory animal species including but not limited to nonhuman primates, horse, pig, mouse, rat, guinea pig, cow and cat. Previously, accurate measurements of thyroid hormones were not possible for many of these species. The assay can thus be used to screen valuable racing and working horse stock as well as pleasure horses for the presence of thyroid autoantibody.

The method of the disclosure is particularly useful in screening assays which may be performed in a general laboratory or a clinical setting more efficiently and without the need of highly trained staff, which are needed because the available sophisticated quantitative assays are performed only in large biomedical and commercial laboratories. The assay of the subject disclosure may be performed simply in both veterinary hospitals and veterinary laboratories to demonstrate the presence of thyroid autoantibodies in serum, thus assisting in the laboratory diagnosis of thyroid disease.

In each of the methods discussed above, the autoantibodies which are initially contacted with the sample may be attached to an immunological or physical reaction surface. An immunological reaction surface is a surface which is insoluble in the reacting medium and on which immunological reactions take place. Typically they are glass, paper, or plastic, such as polystyrene or polyacrylate. The surface may be the interior surface of a test tube, the well of a micro titer plate or some other container suitable for an immunological reaction. Physical reaction surfaces include glass or other types of beads or the walls of a test tube or other surface.

Other appropriate surfaces on which immunological or physical reactions can take place and which can be used, e.g. glass or plastic beads or rods, or paper strips. An immunological or physical reaction surface is one to which the antigens and antibodies adhere.

Immunological and physical reaction conditions for the disclosed methods are for instance conditions with respect to temperature, concentration, solvent, time of contact, and pH under which the immunological or physical reaction such as the formation of an antibody-antigen-autoantibody complex occurs. Those skilled in the art are familiar with the parameters under which such complexes form. The temperature cannot be so high or the pH too extreme as to inactivate the reactant. The solvent is typically a selected buffer or other carrier for the reactants. The reaction products, including the intermediate reaction products of this disclosure, are soluble in the reaction solvent.

In each of the methods disclosed above, the detectable marker is preferably an enzyme, but those skilled in the art to which the subject disclosure pertains would readily understand that other detectable markers may also be used. These include, but are not limited to, luminescent probes, radioisotopes, chromophores, fluorophores, or heavy metals. Enzymes are horseradish peroxidase and alkaline phosphatase, although other enzymes known to those skilled in the art can also be used in the subject disclosure.

The color detectors are most convenient for utilizing the antithyroid autoantibody of the disclosure, but the disclosure is not so limited. Other detection systems including radioisotopic, luminescent, or electrochemical labels can also be employed.

The samples which can be analyzed using the methods of the subject disclosure can be obtained from any vertebrate species in which one is interested in determining the content of thyroid autoantibodies in the sample.

The sample which is analyzed using the subject disclosure is preferably a biological fluid. Numerous other biological fluids from any vertebrate species can be used in the assay. In embodiments of the disclosure, however, the biological fluid comprises serum.

Numerous types of assays can be used in the disclosure as long as the configuration of the assay allows the autoantibodies to recognize the antibody:antigen complex, although the embodiment of the subject disclosure comprises using the modified precipitation or binding assay which allows the autoantibodies of the subject disclosure to recognize the antibody antigen.

Those skilled in the art would readily understand that any conventional immunoassay which would allow the recognition of the antibody:antigen can be used in the disclosure to both quantitatively and qualitatively detect thyroid autoantibodies in non-human species. Such other assays includes regular precipitation assays wherein an antigen is precipitated or bound between the bound autoantibodies on a solid carrier and non-radioisotopic labeled autoantibodies, reverse precipitation assays, in which a non-radioisotopic labeled autoantibodies are reacted with the antigen prior to contact with the bound autoantibodies, and a simultaneous precipitation or binding assay, in which the antibodies and the antigen are reacted simultaneously.

The process of this disclosure utilizes antibodies in new qualitative and quantitative tests to permit immunologic measurement of thyroid autoantibodies. The process is particularly useful in screening assays which may be performed in a general laboratory or clinical setting without the need of expensive equipment or a highly trained staff. Further the direct assay system, such as the CLA, of the disclosure permits for assaying small molecules such as hormones with a high level of specificity and sensitivity and efficiency. The disclosed system provides for a fast and efficient through put in a laboratory or clinical setting.

The assay of the subject disclosure solves a long-standing problem which has not been recognized by those working in the area of thyroid autoantibodies. The problem relates to the need for an assay which can be used to qualitatively and quantitatively detect thyroid autoantibodies antigen in multiple species without using radioisotopes and without the need to create or purchase an assay which is specific for each individual species, for example, rat, rabbit, guinea pig, mouse, etc. It is impractical in the research area to have individual thyroid assays for each species that may need thyroid function testing.

The diagnostic systems of the subject disclosure unexpectedly solve this long-standing problem which has previously been unrecognized in the thyroid hormone diagnostic field. This assay will be of particular use in work where clinicians can evaluate thyroid autoantibodies with a fast and efficient assay useful for each of these species.

The assay of the subject disclosure is more sensitive than previous RIA assays for thyroid function, and is safer (non-radioisotopic reagents), thus providing a definite advantage over the previously used conventional assays.

Those skilled in the art will recognize the foregoing outline as a description of a modified procedure. The generalized outline omits certain of the specific steps such as serial dilution and washing with appropriate buffers which are standard in the procedure. Although specific buffers and other thyroid assay reagents agents are described, and specific dilutions are employed to illustrate the disclosure, these are only illustrative and many equivalents are possible.

The method is employed to determine whether non-humans are at risk to disease caused by inherited or acquired thyroid disease, or for genetically transmitting thyroid disease. It can also be used to measure thyroid levels in non-human individuals experiencing or at risk to develop conditions such as thrombotic states, cancers, or other autoimmune diseases and acute and chronic inflammatory disorders.

The assays of the disclosure have greatly improved sensitivity and specificity, and can be used to detect both antibodies and autoantibodies produced in small amounts in response to exposure to antigens, e.g., non-human thyroid hormone antibodies and autoantibodies.

The disclosure is not limited to the embodiments described as examples. Many different variations in size and scope and features are possible. A person of ordinary skill in the art will recognize that many further combinations and permutations of the present disclosure are possible. For instance, instead of the direct chemiluminescent technique, the system can operate with other non-radio immunoassays such as an immunofluorescent technique.

The disclosure embraces all such alterations, combinations, modifications, and variations that fall within the spirit and scope of the appended claims. The disclosure includes any and all embodiments of the following claims.

What is claimed is:

1. A non-radioisotopic method of determining canine T3AA in a patient sample comprising:
    (a) measuring the amount of Free T3 in a patient sample, wherein the sample is from a canine species, the Free T3 being attached as Free T3/T3AA complex when T3AA is present in the patient sample together with Free T3 unattached to T3AA;
    (b) treating the patient sample with a non-radioisotopic precipitating or binding agent to precipitate or bind Free T3/T3AA complex thereby forming a complex of precipitated or bound Free T3/T3AA complex;
    (c) suspending the non-radioisotopic precipitate or bound complex, and at least one of:
        (i) measuring the amount of Free T3/T3AA complex in suspended non-radioisotopic precipitate or bound complex using a non-radioisotopic label, and
        (ii) subtracting the measurement of i) from a) wherein the result of ii) is directly proportional to the amount of Free T3/T3AA complex thereby determining the amount of T3AA in the patient sample;
    or
        (iii) measuring Free T3 in supernatant or surrounding fluid of the non-radioisotopic precipitate or bound complex using a non-radioisotopic label;
        (iv) subtracting the measurement of iii) from a) wherein the result of iv) is indirectly proportional to the amount of Free T3/T3AA complex thereby determining the amount of T3AA in the patient sample; and
    effecting detection with a sensitivity in a range between 1 picogram per mL and up to about 1 femtogram per mL.

2. A non-radioisotopic method of determining canine T3AA in a sample:
    (a) measuring the amount of Free T3 in a patient sample, wherein the sample is from a canine species, the Free T3 being attached as Free T3/T3AA complex when T3AA is present in the patient sample together with Free T3 unattached to T3AA;
    (b) treating the patient sample with a non-radioisotopic precipitating or binding agent to precipitate or bind Free T3/T3AA complex thereby forming a complex of precipitated or bound FreeT3 and T3AA;
    (c) suspending the non-radioisotopic precipitate or bound complex, and at least one of:
        (i) measuring the amount of Free T3/T3AA complex in suspended non-radioisotopic precipitate or bound complex using a non-radioisotopic label; and
        (ii) subtracting the measurement of i) from a) wherein the result of ii) is directly proportional to the amount of Free T3/T3AA complex thereby determining the amount of T3AA in the patient sample;
    or
        (iii) measuring Free T3 in supernatant or surrounding fluid of the precipitate or bound complex using a non-radioisotopic label; and
        (iv) subtracting the measurement of iii) from a) wherein the result of iv) is indirectly proportional to the amount of FreeT3/T3AA complex thereby determining the amount of T3AA in the patient sample; and
    effecting detection of a), c) i) or c) iii) by employing non-radioisotopic chemiluminescence, and including a bioluminescent detector and microparticles for immobilizing Free T3 as a solid phase, thereby to obtain a non-radioisotopic determination of T3AA.

3. A non-radioisotopic method of determining canine T3AA in a sample
    (a) measuring the amount of Free T3 in a patient sample, wherein the sample is from a canine species, the Free T3 being attached as Free T3/T3AA complex when T3AA is present in the patient sample together with Free T3 unattached to T3AA;
    (b) treating the patient sample with a non-radioisotopic precipitating or binding agent to precipitate or bind FreeT3/T3AA complex thereby forming a complex of precipitated or bound FreeT3 and T3AA;
    (c) suspending the non-radioisotopic precipitate or bound complex, and at least one of:

(i) measuring the amount of Free T3/T3AA complex in suspended non-radioisotopic precipitate or bound complex using a non-radioisotopic label, and (ii) subtracting the measurement of i) from a) wherein the result of ii) is directly proportional to the amount of FreeT3/T3AA complex thereby determining the amount of T3AA in the patient sample;

or (iii) measuring Free T3 in supernatant or surrounding fluid of the precipitate or bound complex using a non-radioisotopic label; and (iv) subtracting the measurement of iii) from a) wherein the result of iv) is indirectly proportional to the amount of FreeT3/T3AA complex thereby determining the amount of T3AA in the patient sample; and (d) effecting detection of a), c) i) or c) iii) by employing a non-radioisotopic detection thereby to obtain a non-radioisotopic determination of T3AA.

4. The method as claimed in claim 2 including measuring Free T3 by both of steps i) and ii) and steps iii) and iv).

5. The method as claimed in claim 3 including measuring Free T3 by both of steps i) and ii) and steps iii) and iv).

6. The method as claimed in claim 1 including measuring Free T3 by both of steps i) and ii) and steps iii) and iv).

7. The method as claimed in claim 1 including measuring, in the step of c) i) T3AA complex in the precipitate or a detachable bound complex, or in the step of c)iii), the Free T3, the measuring being by fluorescence, chemical or other tagging, or measuring the mass.

8. The method as claimed in claim 1 including employing direct chemiluminescence, and including a bioluminescent detector and microparticles for immobilizing Free T3 and having a non-radioisotopic label for detection as a solid phase, the detection of the amount of Free T3 being with a sensitivity more than 1 picogram per mL and being a sensitivity of at least up to about 1 femtogram per mL.

9. The method as claimed in claim 2 the detection range being with a sensitivity between 1 picogram per mL and up to about 1 femtogram per mL.

10. The method as claimed in claim 3 including effecting detection of T3AA complex of step a), c) i) or the Free T3 of c) iii) by detecting with sensitivity in a range between 1 picogram per mL up to 1 femtogram per mL.

11. The method as claimed in claim 1 including having a specificity of the assay at a level at least as specific as an assay performed by known radioimmunoassay technique.

12. The method as claimed in claim 2 including effecting detection by detecting with a sensitivity range between 1 picogram per mL and up to 1 femtogram per mL, and having a specificity of the assay at a level at least as specific as an-assay performed by known radioimmunoassay technique.

13. The method as claimed in claim 3 including effecting detection by detecting with a sensitivity range between 1 picogram per mL and up to 1 femtogram per mL, and having a specificity of the assay at a level at least as specific as an-assay performed by known radioimmunoassay technique.

* * * * *